(12) United States Patent
Naka et al.

(10) Patent No.: US 6,991,366 B2
(45) Date of Patent: Jan. 31, 2006

(54) THERMAL CONDUCTIVITY MEASUREMENT METHOD AND INSTRUMENT AND METHOD OF PRODUCING A HEAT INSULATING MATERIAL

(75) Inventors: Reishi Naka, Asahi (JP); Masato Hayashi, Asahi (JP); Tomohiro Koyama, Asahi (JP); Toshikazu Hasegawa, Shinjuku-ku (JP); Takeshi Aoshima, Hino (JP)

(73) Assignees: Nisshinbo Industries, Inc., Tokyo (JP); EKO Instruments Trading Co., Ltd., Tokyo (JP)

( * ) Notice: Subject to any disclaimer, the term of this patent is extended or adjusted under 35 U.S.C. 154(b) by 0 days.

(21) Appl. No.: 10/004,538

(22) Filed: Oct. 23, 2001

(65) Prior Publication Data

US 2002/0136261 A1    Sep. 26, 2002

(30) Foreign Application Priority Data

Oct. 26, 2000   (JP)   ............................. 2000-327333

(51) Int. Cl.
   *G01K 3/14*   (2006.01)
   *G01N 25/00*   (2006.01)

(52) U.S. Cl. .................. 374/44; 374/137; 73/25.03
(58) Field of Classification Search ............ 374/29–30, 374/44, 50, 111–112, 45, 135, 137; 73/25.01, 73/25.03

See application file for complete search history.

(56) References Cited

U.S. PATENT DOCUMENTS

| | | | |
|---|---|---|---|
| 3,075,377 A * | 1/1963 | Lang ........................... 374/44 |
| 3,114,255 A * | 12/1963 | Niven .......................... 374/44 |
| 3,263,485 A * | 8/1966 | Parviz Mahmoodi ........ 374/44 |
| 3,657,644 A * | 4/1972 | Beam et al. ............... 324/61 R |
| 3,720,103 A * | 3/1973 | Adams et al. ............ 73/190 H |
| 3,733,887 A * | 5/1973 | Stanley et al. .............. 73/15 A |
| 3,745,460 A * | 7/1973 | Belzer et al. ............ 324/158 T |
| 3,971,246 A | 7/1976 | Sumikama et al. ......... 73/15 A |
| 4,236,403 A * | 12/1980 | Poppendiek ................. 374/44 |
| 4,264,423 A * | 4/1981 | Negas et al. ............. 204/195 S |
| 4,553,852 A * | 11/1985 | Derderian et al. ............. 374/1 |
| 4,630,938 A * | 12/1986 | Piorkowska-Palczewska et al. ........................... 374/44 |
| 4,696,578 A * | 9/1987 | Mansuria et al. ............. 374/45 |
| 4,896,281 A * | 1/1990 | Mack ......................... 364/357 |
| 4,929,089 A * | 5/1990 | Tsuchida ..................... 374/44 |
| 5,005,985 A * | 4/1991 | Piokkowska-Galeska et al. ........................... 374/44 |
| 5,112,136 A * | 5/1992 | Sakuma et al. ............... 374/44 |

(Continued)

FOREIGN PATENT DOCUMENTS

DE    2724846 A1    12/1978

(Continued)

OTHER PUBLICATIONS

Thin Film Thermal Conductivity Mater, Amer et al. 1997.*

(Continued)

*Primary Examiner*—Gail Verbitsky
(74) *Attorney, Agent, or Firm*—Seed IP Law Group PLLC

(57) ABSTRACT

A method of measuring the heat conductivity of an object to be measured, comprising generating heat between the object to be measured and a heat resistant material, causing heat to flow through the interior of the object to be measured and the interior of the heat resistant material and obtaining the heat conductivity of the object to be measured from a temperature difference between at least two points of the heat resistant material, a heat conductivity measuring instrument using the same and a method of producing a heat insulating material.

11 Claims, 5 Drawing Sheets

U.S. PATENT DOCUMENTS

| | | | |
|---|---|---|---|
| 5,251,980 A * | 10/1993 | Hiraoka et al. | 374/7 |
| 5,297,868 A * | 3/1994 | Graebner | 374/44 |
| 5,393,351 A * | 2/1995 | Kinard et al. | 136/225 |
| 5,667,301 A * | 9/1997 | Jurkowski et al. | 374/43 |
| 5,881,208 A * | 3/1999 | Geyling et al. | 392/418 |
| 5,940,784 A * | 8/1999 | El-Husayni | 702/130 |
| 6,039,471 A * | 3/2000 | Wyland | 374/43 |
| 6,183,128 B1 * | 2/2001 | Beran et al. | 374/44 |
| 6,190,039 B1 * | 2/2001 | Yaguchi | 374/164 |
| 6,278,051 B1 * | 8/2001 | Peabody | 136/225 |
| 6,331,075 B1 * | 12/2001 | Amer et al. | 374/44 |
| 6,663,278 B1 * | 12/2003 | Chien et al. | 374/43 |
| 2002/0085615 A1 * | 7/2002 | Nakamura et al. | 374/12 |
| 2003/0072349 A1 * | 4/2003 | Osone et al. | 374/43 |
| 2003/0152132 A1 * | 8/2003 | Pipe et al. | 374/137 |
| 2005/0105584 A1 * | 5/2005 | Ichikawa et al. | 374/44 |

FOREIGN PATENT DOCUMENTS

| | | | |
|---|---|---|---|
| JP | 61198046 | 9/1986 | |
| JP | 62172248 A * | 7/1987 | 374/44 |
| JP | 01013445 A * | 1/1989 | |
| JP | 4155173 | 5/1992 | |
| JP | 5142075 | 6/1993 | |
| JP | 7294359 | 11/1995 | |
| JP | 2610250 | 5/1997 | |

OTHER PUBLICATIONS

Assessment of heat Flow through Bulk geologic Material, Green et al. Joint Conferences. 1997.*

Development of NPL Guarded Hot Plate Emissometer, Stacey et al. Joint Conferences. 1997.*

* cited by examiner

THERMAL CONDUCTIVITY MEASUREMENT METHOD AND INSTRUMENT AND METHOD OF PRODUCING A HEAT INSULATING MATERIAL

BACKGROUND OF THE INVENTION

1. Field of the Invention

The present invention relates to the measurement of the heat conductivity of a material and the production of a heat insulating material.

2. Description of the Related Art

Heretofore, heat conductivity has been measured by a plate comparison method specified in JIS A 1412. That is, a test sample and a reference plate are placed one upon the other, a temperature difference is given to them, the difference in surface temperature between them is measured, and the heat conductivity of the test sample is obtained from the ratio and the heat conductivity of the reference plate. In the case of a vacuum insulation material, the heat conductivity of the vacuum insulation material is measured by a so-called reverse vacuum method that it is inspected visually whether the vacuum insulation material swells when the vacuum insulation material is placed in vacuum in a container.

However, the plate comparison method requires a steady state. It takes about 1 hour to reach the steady state, thereby providing an appropriate condition to measure thermal conductivity. Accordingly, it is difficult to measure a large number of products in a short term. With the reverse vacuum method, accurate heat conductivity cannot be measured and when air is contained gradually, it is difficult to judge visually.

BRIEF SUMMARY OF THE INVENTION

It is an object of the present invention to measure heat conductivity in a short period of time.

It is another object of the present invention to measure the heat conductivity of even a vacuum insulation material with ease.

It is still another object of the present invention to produce a heat insulating material having heat conductivity within a predetermined range.

According to a first aspect of the present invention, there is provided a method of measuring the heat conductivity of an object to be measured, comprising generating heat between the object to be measured and a heat resistant material, causing heat to flow through the interior of the object to be measured and the interior of the heat resistant material, and obtaining the heat conductivity of the object to be measured from a temperature difference between at least two locations on the heat resistant material.

According to a second aspect of the present invention, there is provided a method of measuring the above heat conductivity, wherein the heat generation area is divided into a central area and an area surrounding the central area.

According to a third aspect of the present invention, there is provided a method of measuring the above heat conductivity, wherein the externally exposed surface of the heat resistant material is covered with a cover member.

According to a fourth aspect of the present invention, there is provided an instrument for measuring the heat conductivity of an object to be measured, comprising a heat resistant material having heat resistance, a temperature difference measuring unit capable of measuring a temperature difference between two locations on the heat resistant material, and a heat generating unit placed on the surface of the heat resistant material, wherein the heat resistant material is placed such that the heat generating unit comes in contact with the surface of the object to be measured, and the heat conductivity of the object to be measured is obtained from a temperature difference between two locations on the heat resistant material.

According to a fifth aspect of the present invention, there is provided an instrument for measuring the above heat conductivity, wherein the heat generating unit comprises a main heat generating section for generating heat in a central area, and an auxiliary heat generating section for generating heat in an area surrounding the main heat generating section.

According to a sixth aspect of the present invention, there is provided a method of producing a heat insulating material whose heat conductivity is measured, comprising generating heat between the heat insulating material and a heat resistant material, causing heat to flow through the interior of the heat insulating material and the interior of the heat resistant material and obtaining the heat conductivity of the heat insulating material from a temperature difference between at least two locations on the heat resistant material.

According to a seventh aspect of the present invention, there is provided a method of producing a heat insulating material, wherein the heat generation area is divided into a central area and an area surrounding the central area.

BRIEF DESCRIPTION OF THE SEVERAL VIEWS OF THE DRAWING(S)

The above and other objects of the present invention will become readily apparent by reference to the following detailed description when considered in conjunction with the accompanying drawings wherein.

DETAILED DESCRIPTION OF THE INVENTION

Embodiments of the present invention will be described hereinbelow with reference to the accompanying drawings.

Figure 1:
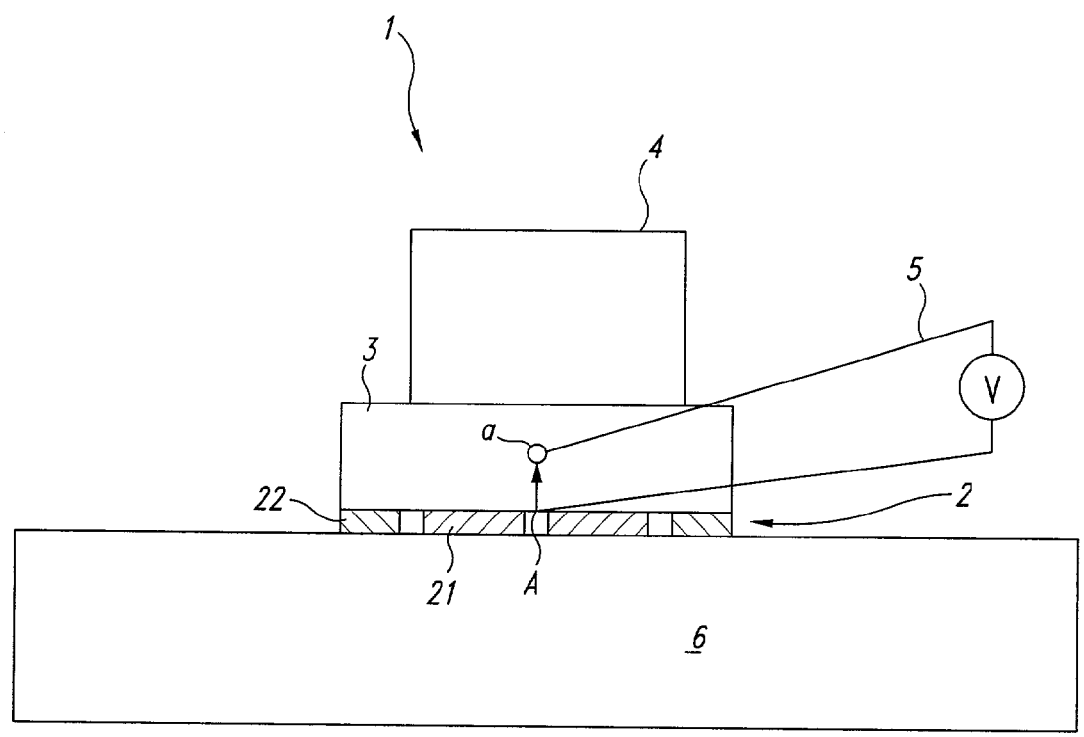
FIG. 1 is a schematic diagram of a system for the measurement of heat conductivity according to an embodiment of the present invention.

The heat conductivity measuring instrument 1 measures the heat conductivity of an object 6 to be measured, such as a heat insulating material, by contacting the object. For example, as shown in FIG. 1, the heat conductivity measuring instrument 1 comprises a heat resistant material 3 and a heat generating unit 2. The heat resistant material 3 is used to measure an internal temperature difference. The heat insulating material can include a vacuum insulation material.

Heat is generated between the object 6 to be measured and the heat resistant material 3 by the heat generating unit 2 and flows through the object 6 to be measured and the heat resistant material 3. The heat conductivity of the object 6 to be measured can be obtained from a temperature difference produced by a heat flow 31 (FIG. 2) flowing through the interior of the heat resistant material 3. For example, when the heat conductivity of the object 6 to be measured is high, the amount of heat flowing through the heat resistant material 3 becomes small, whereby the internal temperature difference of the heat resistant material 3 becomes small. On the contrary, when the heat conductivity of the object 6 to be measured is low, the amount of heat flowing through the heat resistant material 3 becomes large, whereby the internal temperature difference of the heat resistant material 3 becomes large. Using this principle, the heat conductivity of the object 6 to be measured can be measured indirectly.

Any material is acceptable as the heat resistant material 3 if a temperature difference is produced between two points of the heat resistant material when a heat flow 31 is existent. For example, super silica may be used as the heat resistant material 3. Super silica is an inorganic material which is hardly changed by temperature variations and has a heat conductivity of 0.0438 W/mK (when dried).

Figure 2:
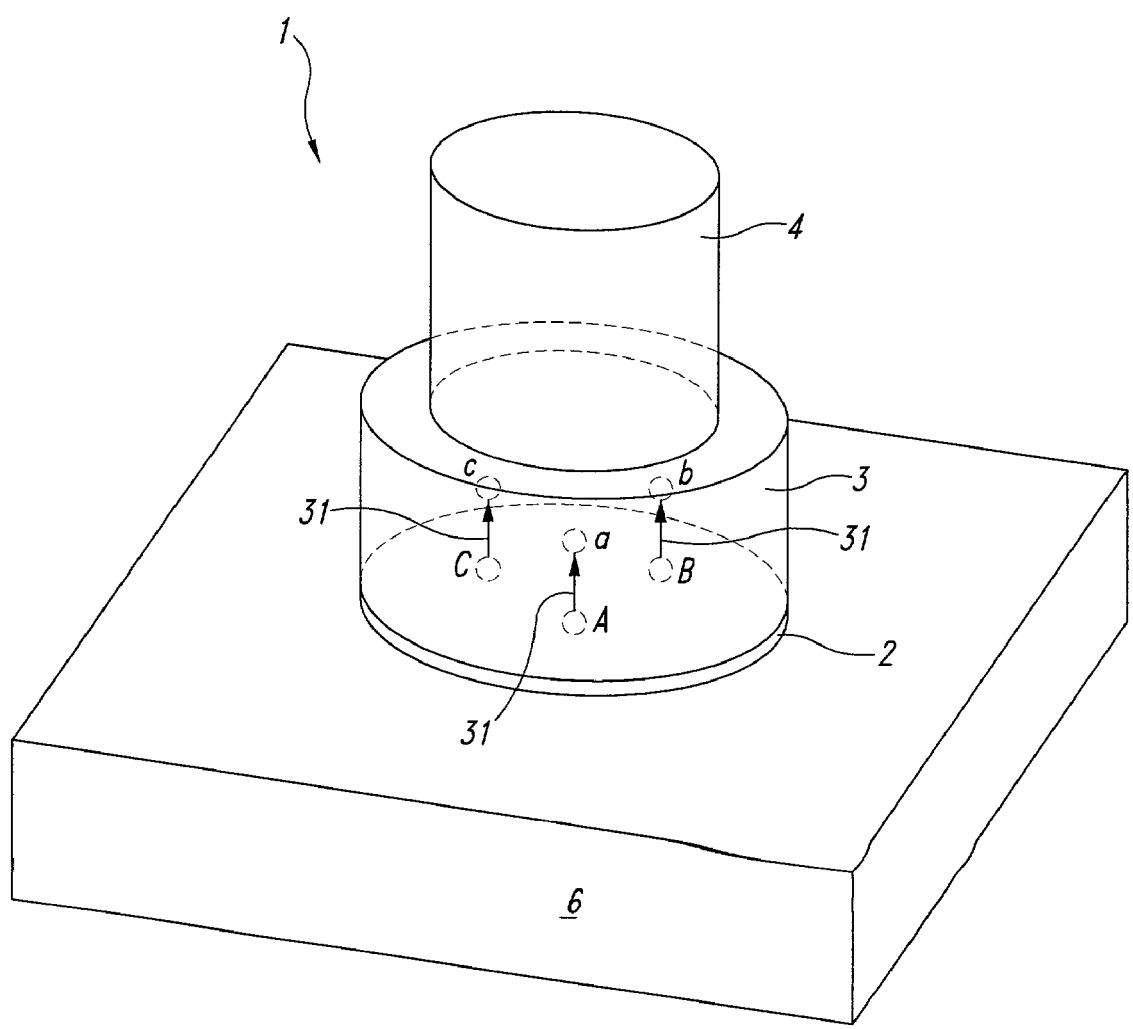
FIG. 2 is an isometric view of a heat conductivity measuring instrument according to an embodiment of the present invention.

A temperature difference measuring unit 5 for measuring a temperature difference between at least two locations within the interior of the heat resistant material 3 is placed in the interior of the heat resistant material 3. In FIG. 2, the temperature difference between two points is measured at three pairs of locations (A, a), (B, b) and (C, c) to increase accuracy. When the locations of the two points to be measured to obtain temperature differences are spaced apart in the direction of the heat flow 31, a temperature difference is easily measured. For example, three locations (A, B, C) are on the surface in contact with the heat generating unit 2 and the other three locations (a, b, c) are spaced vertically from the three locations (A, B, C) as oriented in FIG. 2.

Any temperature difference measuring unit is acceptable as the temperature difference measuring unit 5 (FIG. 1) if it can measure a temperature difference between two points. For example, a thermocouple may be used. The thermocouple is, for example, of a constantan type, made from copper-constantan, consists of three pairs connected in series, and has a line diameter of 0.1 mm and a resistance value of 15 Ω. Cold contact points are located in the interior of the heat resistant material (for example, 20 mm away from the heat generating unit). Hot contact points are located at three locations (A, B, C) which are equally spaced apart on the top of the main heat generating section 21 (FIG. 3) of the heat generating unit 2.

Figure 3:
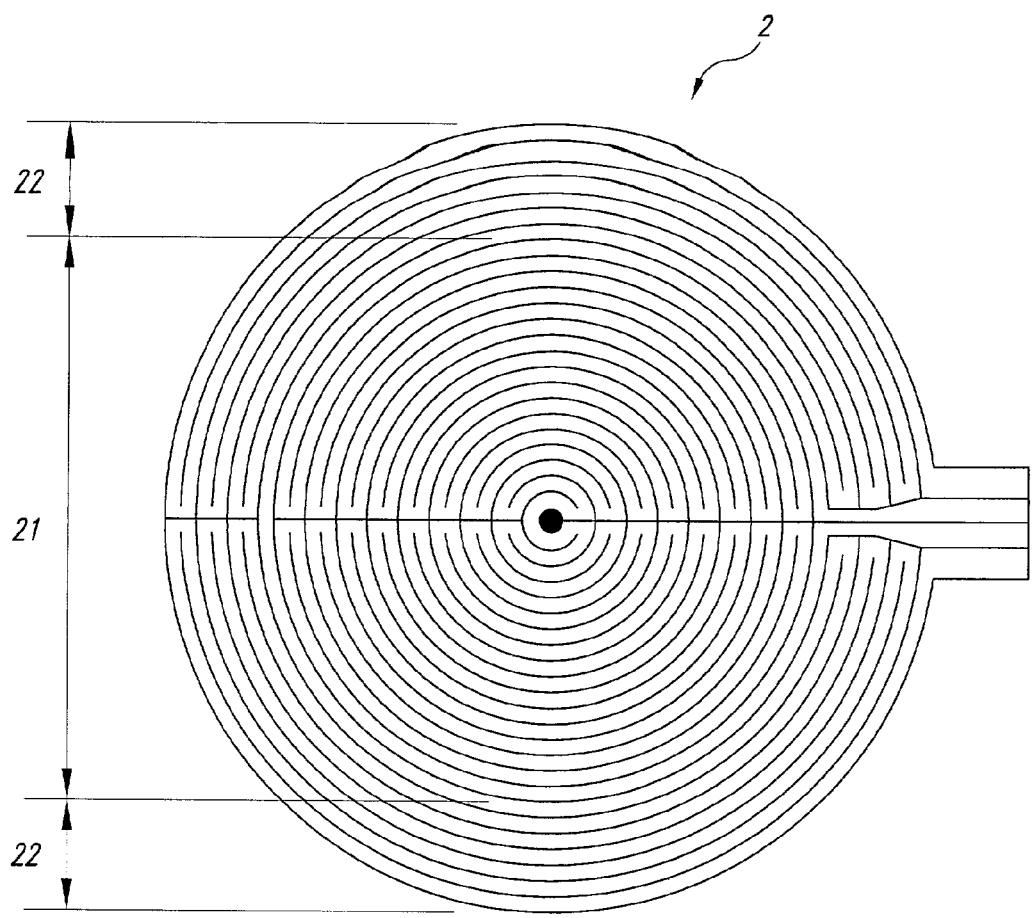
FIG. 3 is a plan view of a heat generating unit from the instrument of FIG. 2.

Any heat generating unit is acceptable as the heat generating unit 2 if it can be interposed between the object 6 to be measured and the heat resistant material 3, and can transmit heat to the interior of the object 6 to be measured and the interior of the heat resistant material 3. As shown in FIG. 3, the heat generating unit 2 has a double structure consisting of a main heat generation section 21 for generating a heat flow to be measured, and an auxiliary heat generating section 22, located around the main heat generating section, for preventing a heat bridge in a transverse direction. If the heat bridge in a transverse direction can be prevented, only the main heat generating section 21 will suffice.

The heat generating unit 2 can be made of a thin film formed by joining together a cover layer and a constantan sheet and forming a heater pattern by etching. In the illustrated embodiment, the main heater of the main heat generating section 21 has an outer diameter of 28 mm, an internal resistance of about 45 Ω, and a supply current of 100 mA. The guard heater of the auxiliary heat generating section 22 is arranged in loop around the main heater and has a width of 6 mm, an internal resistance of about 45 Ω, and a supply current of 100 mA.

Figure 4:
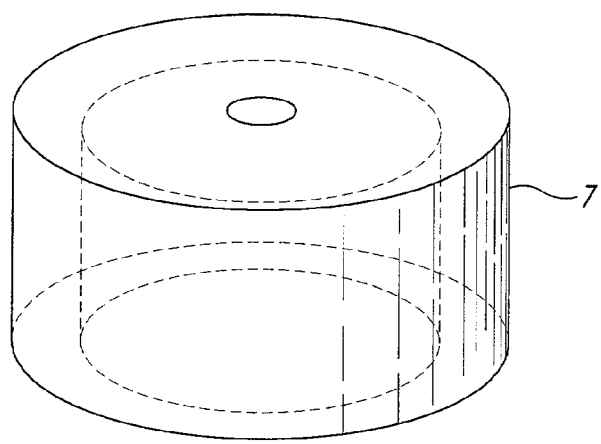
FIG. 4 is a perspective view of a cover member according to an embodiment of the present invention.

The cover member 7 (FIG. 4) is used to cover the heat resistant material 3 in order to prevent the deterioration of the surface of the heat resistant material 3 and the influence of external ambient temperature. The cover member 7 is, for example, an acrylic cover having a heat conductivity of about 1.00 W/mK. A material which does not have too high conductivity unlike metal or too low conductivity unlike a heat insulating material is suitable. The cover member 7 is, for example, shaped like a cylindrical cover for covering the heat resistant material 3 from above as shown in FIG. 4. The outer diameter of this cylinder is 50 mm and the height thereof is 30 mm. The top portion of the cover member has a thickness of 5 mm and a hole having a diameter of 6 mm in the center. The side portion of the cover member has a thickness of 5 mm.

Any close contact aid material is acceptable as the close contact aid material 4 (FIG. 2) if it enables close contact among the heat resistant material 3, the heat generating unit 2 and the object 6 to be measured. The close contact aid material 4 is, for example, a brass weight placed on the heat resistant material 3 to enable close contact among the heat resistant material 3, the heat generating unit 2 and the object 6 to be measured by gravitation. Other biasing means can be substituted for the close contact aid material.

Figure 5:
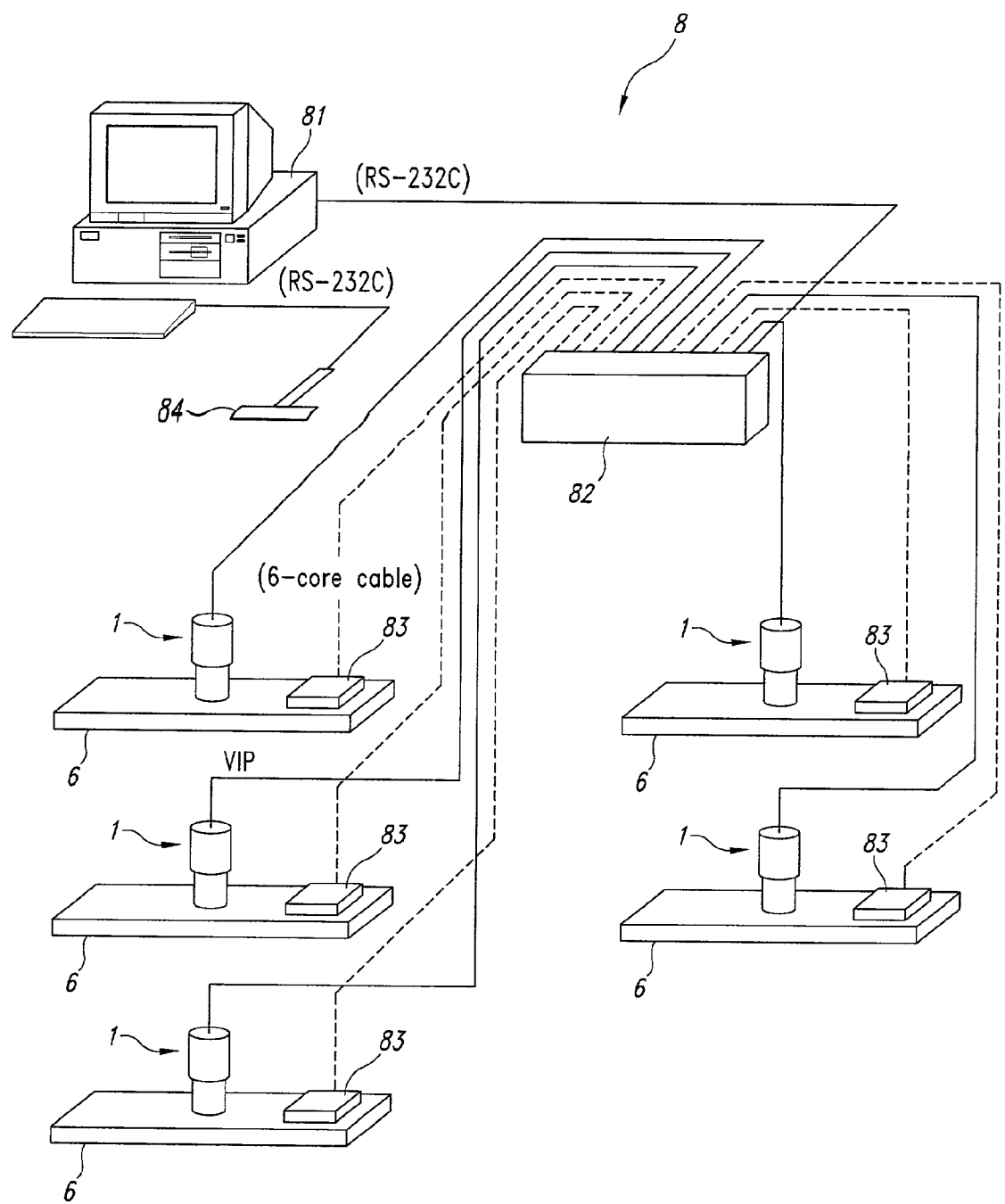
FIG. 5 is a diagram for explaining a heat conductivity measuring system according to an embodiment of the present invention.

The heat conductivity measuring system 8 measures the object 6 to be measured using the heat conductivity measuring instrument 1. For example, as shown in FIG. 5, it has a plurality of stages to measure the object 6 to be measured on each stage. The heat conductivity measuring instrument 1 and a display unit 83 which displays the state of measurement are placed on each stage. The heat conductivity measuring instrument 1 and the display unit 83 are electrically connected to a metering unit 82 and further to a personal computer 81 by RS-232C. The heat conductivity measuring system 8 can incorporate a bar code reader 84 as required to read a bar code attached to the object 6 to be measured to automatically identify a heat insulating material which is the object 6 to be measured.

The display unit 83 displays the start of heat conductivity measurement and the state of the heat conductivity measuring instrument 1, for example, "measuring", "cooling", "out of operation", "stand-by", "measurable" and "the result of measurement". The judgment of the measurement result is carried out by the personal computer 81 and then displayed on the display unit 83 such as a lamp.

The metering unit 82 controls the display of the display unit 83 and the current of the heat generating unit 2 of the heat conductivity measuring instrument 1 and transfers the output of the temperature difference measuring unit 5 to the personal computer over RS-232C. A terminal base is used to connect the heat conductivity measuring instrument 1, to the metering unit 82. The metering unit 82 detects the disconnection of the heat conductivity measuring instrument 1 as well. The metering unit 82 has two constant current generating units for each stage to supply constant current, for example, 100 mA to the main heat generating section 21 and the auxiliary heat generating section 22.

The personal computer 81 incorporates a program to display the result of measurement, input bar codes and store the result of measurement. The personal computer 81 performs the control of information from the metering unit 82, the heat conductivity measuring instruments and the bar code reader 84, and transfers data in the organization by LAN or other network as required. The stored measurement data include the production numbers of the objects to be measured, the stage numbers of the measuring heat conductivity measuring instruments, measurement values, measurement times and the results of judgment.

An embodiment of the method of measuring heat conductivity will be described hereinbelow.

The personal computer 81 and the metering unit 82 are powered on to input a stand-by voltage range (±0.05 mV), stand-by time (30 sec) and reference value (3.847 mV) into the personal computer 81. At this point, the display unit 83 displays "out of operation", "stand-by" or "cooling".

The personal computer 81 reads a bar code given to the object 6 to be measured. At this point, the display unit 83 displays "measurable". The heat conductivity measuring instrument 1 is placed near the center of the surface of the object 6 to be measured and the "start" button is depressed. At this point, the display unit 83 displays "measuring".

The personal computer 81 counts the measuring time and terminates measurement after a predetermined duration, such as 120 seconds. At this point, the display unit 83 displays "cooling". When the output voltage of the thermocouple of the temperature difference measuring unit 5 is higher than the reference value, that is, 3.847 mV or more, the object 6 to be measured is accepted. The personal computer 81 and the display unit 83 display the result of judgment.

The temperature difference measuring unit 5 is returned to the top of the brass stage and waits until the voltage returns to a stand-by voltage range. At this point, the display unit 83 displays "cooling". When the voltage falls within the stand-by voltage range, the stand-by time, for example, 30 seconds begins to be counted. At this point, the display unit 83 displays "out of operation". When the voltage does not exceed the stand-by voltage range during the stand-by time, the next measurement is possible. When the voltage exceeds the stand-by voltage range, "cooling" is displayed and it waits until a voltage deviation is gone.

Since the heat conductivity of the object 6 to be measured and the temperature difference of the temperature difference measuring unit 5, that is, the output voltage of the thermocouple are proportional to each other, a proportional constant is measured for each heat conductivity measuring instrument 1 in advance. That is, the calibration of the heat conductivity measuring instrument 1 is carried out.

A large number of objects to be measured are used for calibration as samples whose values are close to a reference value (W/mK) to be set. For example, when the heat conductivity is $6.00 \times 10^{-3}$ W/mK, five objects 6 to be measured whose heat conductivity's are already known are used for calibration. All the six objects 6 to be measured are measured by the heat conductivity measuring instruments 1 two or three times.

Figure 6:
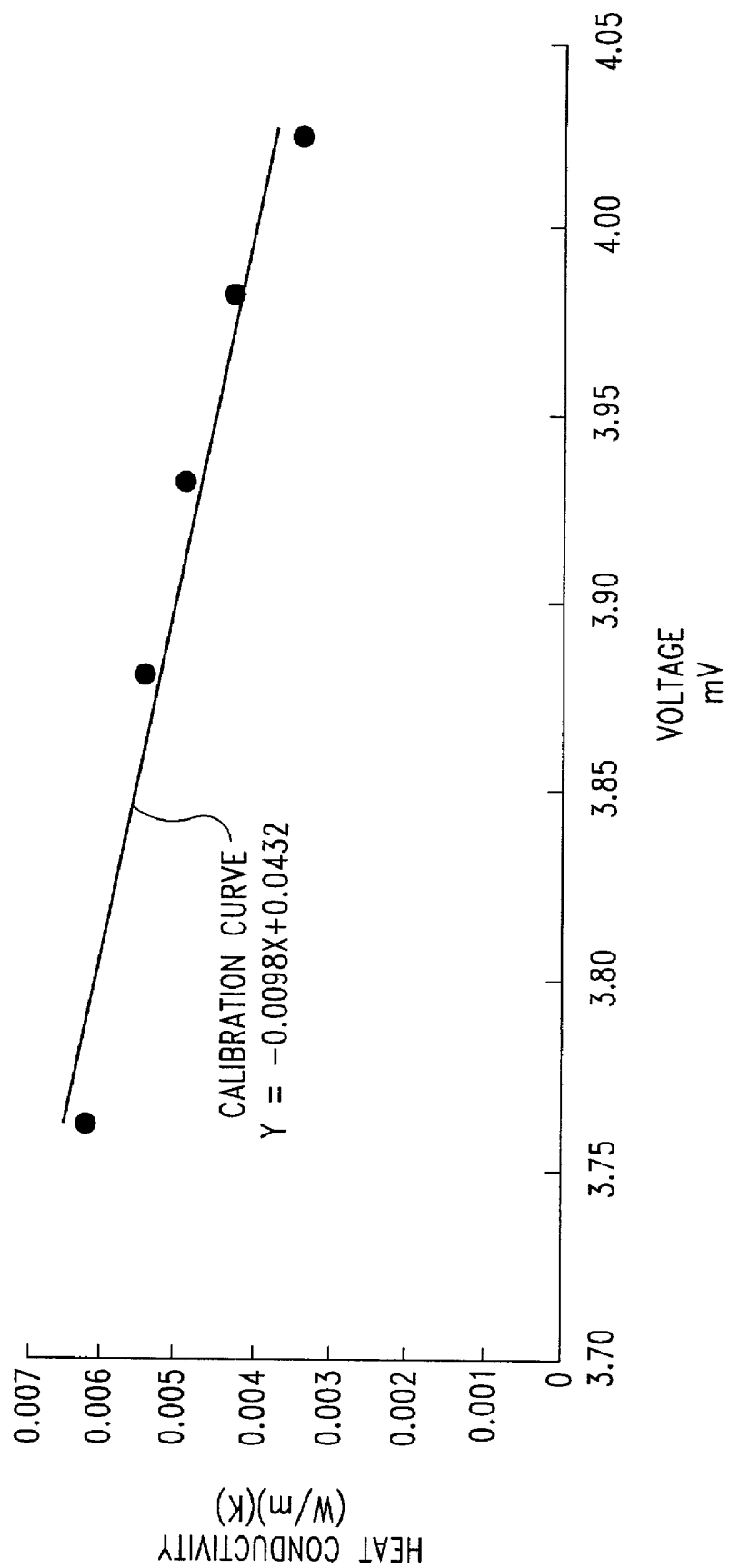
FIG. 6 is a diagram showing a calibration curve.

The mean value of the outputs of the heat conductivity measuring instruments 1 which have measured five objects 6 to be measured is obtained. The result is shown in Table 1. The voltage (mV) is plotted on the axis of abscissa (x axis) and the heat conductivity (W/mK) is plotted on the axis of ordinate (y axis) and FIG. 6 shows a graph obtained by plotting the obtained values. The calibration curve is drawn by connecting the plotted mean values. The calibration curve is a straight line. When the calibration curve of FIG. 6 is expressed by an equation, $y = -0.0098x + 0.0432$.

TABLE 1

| Objects to be measured (No.) | Already known heat conductivity (W/mK) | Voltage value (mV) |
|---|---|---|
| 1 | 0.00352 | 4.025 |
| 2 | 0.00438 | 3.983 |
| 3 | 0.00503 | 3.932 |
| 4 | 0.00548 | 3.880 |
| 5 | 0.00622 | 3.762 |

When the measurement value of the object 6 to be measured is inserted into the previously obtained calibration curve, the heat conductivity can be obtained from the equation, graph and table. The measurement value may be a voltage value when a thermocouple is specified or a temperature difference.

The method of producing a heat insulating material will be described hereinbelow.

When a heat insulating material is to be produced, the heat conductivity of the heat insulating material which is an object to be measured is measured by the above heat conductivity measuring instrument 1, the heat conductivity measuring system 8 or the heat conductivity measuring method.

It is judged whether the heat conductivity of the measured heat insulating material falls within a predetermined range to select acceptable heat insulating materials. Thus, heat insulating materials having heat conductivity within a predetermined range can be obtained. Particularly in the case of a vacuum insulation material comprising a resin or fine powder having open-cells as a core material and coated with a metal film, resin film or a laminate film consisting of a metal and a resin, compared with the conventional plate comparison method or reverse vacuum method, acceptable products can be selected by carrying out a lot of accurate inspections in a short period of time.

The present invention can present a number of advantages. For example, the present invention makes it possible to obtain the heat conductivity of an object to be measured in a short period of time. The present invention makes it possible to measure the heat conductivity of even a vacuum insulation material. Although a heat bridge in a transverse direction easily occurs in a vacuum insulation material coated with a metal film or a laminate film consisting of a metal and a resin, when an auxiliary heat generating section is formed, the heat bridge can be easily prevented and the heat conductivity can be measured accurately in a short period of time. The present invention makes it possible to produce a heat insulating material having heat conductivity within a predetermined range easily.

It is readily apparent that the above-described embodiments have the advantage of wide commercial utility. It should be understood that the specific form of the invention hereinabove described is intended to be representative only, as certain modifications within the scope of these teachings will be apparent to those skilled in the art. Accordingly, reference should be made to the following claims in determining the full scope of the invention.

What is claimed is:

1. A method of measuring a thermal conductivity of an object, comprising:

positioning a heat source between and in contact with a surface of the object and a surface of a heat resistant material;

aligning the object, the heat source, and the heat resistant material along a substantially vertical axis;

causing heat to flow along a heat flow path from the heat source into the object and an interior of the heat resistant material;

measuring a temperature of at least two spaced apart locations aligned substantially parallel to the vertical axis, the locations being against or inside the heat resistant material, within a short period of time substantially less than one hour after first causing the heat to flow; and calculating the thermal conductivity of the object based on the temperature difference between the spaced apart locations as measured within the short period of time.

2. The method of claim 1 wherein the heat source has a central area and an auxiliary area surrounding the central area.

3. The method of claim 1 wherein an externally exposed surface of the heat resistant material is covered with a cover member.

4. An instrument for measuring the thermal conductivity of an object to be measured, comprising:
   a heat resistant material having a heat resistance;
   a temperature difference measuring unit capable of measuring a temperature difference between a surface location spaced apart from a second location of the heat resistant material;
   a heat generating unit configured to be placed vertically between the surface of the heat resistant material and a surface of the object;
   wherein the heat generating unit is configured to generate heat between the surface of the object and the surface of the heat resistant material, causing heat to flow from the surfaces of the object and the heat resistant material to the second location of the heat resistant material;
   the temperature difference measuring unit is configured to measure the temperature difference of the heat resistant material within a short period of time substantially less than one hour after heat is first generated; and
   the thermal conductivity of the object is obtained from the temperature difference, measured within the short period of time, between the surface location and the second location of the heat resistant material, the second location is aligned substantially vertically from the surface location.

5. The instrument of claim 4 wherein the heat generating unit comprises a main heat generating section for generating heat in a central area and an auxiliary heat generating section for generating heat in an area surrounding the main heat generating section.

6. A method of determining a thermal conductivity of a heat insulating material, comprising an inspection step in which heat is generated between the heat insulating material and a heat resistant material and caused to flow through the heat insulating material and the heat resistant material, and a measurement step in which a temperature difference of the heat resistant material is initiated and is terminated after a period of time substantially less than one hour, and the thermal conductivity of the heat insulating material is obtained from a temperature difference between at least two points of the heat resistant material.

7. The method of claim 6 wherein a heat generation area is divided into a central area and an area surrounding the central area.

8. A method of measuring an object's thermal conductivity, of the method comprising:
   generating heat between a surface of the object and a surface of a heat resistant material;
   receiving a first amount of the generated heat at the surface of the object;
   receiving a second amount of the generated heat at the surface of the heat resistant material;
   receiving at least a portion of the second amount of generated heat at a second location of the heat resistant material;
   measuring a temperature difference between the surface location and the second location of the heat resistant material, the second location spaced apart and aligned substantially, vertically parallel to the surface location; and
   calculating the thermal conductivity of the object based on the temperature difference, as measured within a short period of time after heat is initially generated, between the surface location and the second location of the heat resistant material.

9. The method of claim 1 wherein the object is a heat insulating material.

10. The method of claim 1 wherein the object is a vacuum insulation material.

11. The method of claim 1, further comprising steps of predetermining a calibration curve showing a relation between the thermal conductivity and the temperature difference and applying the measured temperature difference to said calibration curve to determine the heat conductivity of the object.

* * * * *